(12) United States Patent
Smith

(10) Patent No.: US 10,219,768 B2
(45) Date of Patent: Mar. 5, 2019

(54) METHOD FOR STANDARDIZING TARGET LESION SELECTION AND TRACKING ON MEDICAL IMAGES

(71) Applicant: EMASS LLC., Ridgeland, MS (US)

(72) Inventor: Andrew Dennis Smith, Hoover, AL (US)

(73) Assignee: EMASS LLC, Ridgeland, MS (US)

( * ) Notice: Subject to any disclaimer, the term of this patent is extended or adjusted under 35 U.S.C. 154(b) by 0 days.

(21) Appl. No.: 16/003,707

(22) Filed: Jun. 8, 2018

(65) Prior Publication Data

US 2018/0353148 A1 Dec. 13, 2018

Related U.S. Application Data

(60) Provisional application No. 62/516,917, filed on Jun. 8, 2017.

(51) Int. Cl.

| | |
|---|---|
| *A61B 5/05* | (2006.01) |
| *A61B 6/00* | (2006.01) |
| *A61B 8/08* | (2006.01) |
| *G06T 11/00* | (2006.01) |
| *G06T 15/08* | (2011.01) |
| *G06T 7/11* | (2017.01) |
| *G16H 30/40* | (2018.01) |

(Continued)

(52) U.S. Cl.

CPC .......... *A61B 6/5217* (2013.01); *A61B 5/055* (2013.01); *A61B 8/5223* (2013.01); *G06T 7/0016* (2013.01); *G06T 7/11* (2017.01); *G06T 11/005* (2013.01); *G06T 15/08* (2013.01); *G16H 30/40* (2018.01); *G06T 2200/24* (2013.01); *G06T 2207/10088* (2013.01); *G06T 2207/10116* (2013.01); *G06T 2207/20092* (2013.01); *G06T 2207/30096* (2013.01); *G06T 2207/30204* (2013.01); *G06T 2210/41* (2013.01); *G06T 2215/16* (2013.01); *G06T 2219/004* (2013.01)

(58) Field of Classification Search
None
See application file for complete search history.

(56) References Cited

U.S. PATENT DOCUMENTS 5,827,942 A * 10/1998 Madsen ................ G01S 7/5205
   73/1.82
7,379,605 B1 * 5/2008 Ticsa .................... G06F 19/321
   382/232

(Continued)

*Primary Examiner* — David H Chu
(74) *Attorney, Agent, or Firm* — Workman Nydegger

(57) ABSTRACT

Systems and methods for standardizing target lesion selection within cross-sectional medical images can include the acts of: (i) sending a plurality of cross-sectional images to a user device, where each cross-sectional image is a cross-sectional slice of digital medical image data captured at a first timepoint from a radiologic device; (ii) receiving a user input identifying a set of pixels corresponding to a target lesion within a cross-sectional image of the plurality of cross-sectional images; and (iii) generating a target lesion location file that includes a precise anatomical location of the cross-sectional image and a pixel location of the target lesion within the cross-sectional image. The systems and methods can additionally include the act of causing a digital marker to be displayed on the cross-sectional image and on each analogous cross-sectional image captured at a later timepoint.

20 Claims, 9 Drawing Sheets

(51) Int. Cl.
*G06T 7/00* (2017.01)
*A61B 5/055* (2006.01)

(56) References Cited

U.S. PATENT DOCUMENTS

| | | | | |
|---|---|---|---|---|
| 8,423,120 B2* | 4/2013 | Tynes | ............ | A61B 5/055 600/424 |
| 2007/0100226 A1* | 5/2007 | Yankelevitz | ......... | A61B 5/1075 600/407 |
| 2008/0027305 A1* | 1/2008 | Gundel | ............ | A61B 6/12 600/407 |
| 2008/0167642 A1* | 7/2008 | Palanker | ............ | A61F 9/008 606/4 |
| 2008/0312959 A1* | 12/2008 | Rose | ............ | G06Q 10/06 705/2 |
| 2009/0129673 A1* | 5/2009 | Simon | ............ | G06T 7/0012 382/173 |
| 2009/0279756 A1* | 11/2009 | Gindele | ............ | G06T 19/00 382/128 |
| 2010/0312096 A1* | 12/2010 | Guttman | ............ | A61B 5/415 600/411 |
| 2012/0253173 A1* | 10/2012 | Endo | ............ | G06T 11/008 600/411 |
| 2012/0308094 A1* | 12/2012 | Harish | ............ | G06F 19/321 382/128 |
| 2013/0148871 A1* | 6/2013 | Kwon | ............ | G06K 9/00 382/128 |
| 2013/0261431 A1* | 10/2013 | Amberg | ............ | A61B 6/12 600/424 |
| 2014/0016845 A1* | 1/2014 | Gazit | ............ | A61B 5/055 382/130 |
| 2014/0164948 A1* | 6/2014 | Joo | ............ | G06F 19/321 715/752 |
| 2014/0212014 A1* | 7/2014 | Kim | ............ | G06T 3/0068 382/131 |
| 2014/0222444 A1* | 8/2014 | Cerello | ............ | G06Q 10/00 705/2 |
| 2014/0241606 A1* | 8/2014 | Park | ............ | G06T 7/0081 382/131 |
| 2014/0254904 A1* | 9/2014 | Matthews | ............ | G06K 9/6212 382/131 |
| 2014/0314288 A1* | 10/2014 | Roychowdhury | .... | G06T 7/0012 382/128 |
| 2015/0126860 A1* | 5/2015 | Beymer | ............ | A61B 6/468 600/431 |
| 2015/0310172 A1* | 10/2015 | Takata | ............ | G16H 50/70 382/128 |
| 2016/0314600 A1* | 10/2016 | Nguyen | ............ | G06T 11/003 |
| 2016/0374644 A1* | 12/2016 | Mauldin, Jr. | ......... | A61B 8/4245 600/424 |
| 2017/0011186 A1* | 1/2017 | Oosawa | ............ | G06T 7/0014 |
| 2017/0100098 A1* | 4/2017 | Urabe | ............ | A61B 8/085 |
| 2018/0098700 A1* | 4/2018 | Prchkovska | ............ | G16H 50/20 |

* cited by examiner

METHOD FOR STANDARDIZING TARGET LESION SELECTION AND TRACKING ON MEDICAL IMAGES

CROSS-REFERENCE TO RELATED APPLICATIONS

This application claims the benefit of U.S. Provisional Patent Application No. 62/516,917, filed Jun. 8, 2017, and entitled "METHOD FOR STANDARDIZING TARGET LESION SELECTION AND TRACKING ON MEDICAL IMAGES," the disclosure of which is incorporated herein by this reference in its entirety.

BACKGROUND

Assessment of changes in tumor burden is an important feature for defining tumor response in clinical trials. Both tumor shrinkage (objective response) and development of disease progression are important endpoints in clinical trials as these often determine objective response, which in turn define time to progression (TTP) and progression-free survival (PFS). In order to standardize tumor response assessment in clinical trials, various response criteria have been described, including Response Evaluation Criteria in Solid Tumors (RECIST) version 1.0 or more commonly version 1.1, modified RECIST (mRECIST), World Health Organization (WHO) Criteria, Choi Criteria, Vascular Tumor Burden (VTB) Criteria, Morphology Attenuation Size and Structure (MASS) Criteria, immune-related Response Criteria (irRC), immune-related RECIST (irRECIST), Cheson Criteria, Lugano Classification lymphoma response criteria, Positron Emission Tomography Response Criteria in Solid Tumors (PERCIST), European Organization for Research and Treatment of Cancer (EORTC) Response Criteria, Response Assessment in Neuro-Oncology (RANO) Criteria, International Myeloma Working Group (IMWG) consensus criteria, etc.

In order to assess objective response, an estimate of the overall tumor burden at baseline is needed and used as a comparator for subsequent measurements. Each tumor response criteria specifies parameters that define a measurable lesion at baseline. For example, RECIST 1.1 defines a non-nodal lesion as measurable if it measures cm in long axis at baseline and defines a lymph node as measurable if it measures cm in short axis at baseline. When one or more measurable lesions are present at baseline, each tumor response criteria specifies which lesions should be considered as target lesions. Target lesions are typically selected based on being the largest in size or most metabolically active but also should lend themselves to reproducible repeated measurements. Most tumor response criteria limit the number of total target lesions and limit the number of target lesions per organ. For example, RECIST 1.1. limits the total number of target lesions to 5 and the total number of target lesions per organ to 2. Each tumor response criteria specifies how the target lesions should be measured. For example, RECIST 1.1 states that non-nodal lesions should be measured in the longest dimension on axial cross-sectional images, while lymph nodes should be measured in short axis on axial cross-sectional images. The total tumor burden is then a mathematical calculation made from the individual target lesions. For example, the sum of the diameters (longest for non-nodal lesions, short axis for nodal lesions) for all target lesions is calculated and reported as the baseline sum diameters per RECIST 1.1.

The baseline measurements are used as a reference to characterize objective tumor regression or progression in the measurable dimension of the disease. All other lesions (or sites of disease) are identified as non-target lesions. The site of disease of all non-target lesions should be recorded at baseline. At subsequent time points, measurement of non-target lesions is not required, and these lesions are typically followed and defined as 'complete response' (CR), 'unequivocal progressive disease' (PD), 'non-CR/non-PD', or 'not evaluable' (NE). Alternatively, the non-target lesions could be qualitatively evaluated, such as 'present', 'absent', 'larger', or 'smaller'.

While most tumor response criteria utilize measured changes in target lesion length or size as a means of defining objective response, some criteria (e.g., PERCIST and EORTC Response Criteria) utilize measured changes in target lesions radiotracer activity as a means of defining objective response, and other criteria use a combination of both. Different tumor response criteria may utilize different metrics, mathematical calculations, or cut points to define objective response, and computers implemented methods that automate one or more processes or method acts and/or ensure user compliance with one or more criteria may be used to reduce errors and improve efficiency in tumor response assessment.

A common method for determining objective response in a phase 2 or 3 industry-sponsored oncologic clinical trial includes a combination of local radiologic review (LRR) and independent central review (ICR). With LRR, local physician reviewers (often a radiologist) generally do not receive training on the protocol or the specific response criteria, multiple different local physician reviewers may interpret the images, different local physician reviewers may choose and measure different target lesions, and local physician reviewers are often unaware of the subject enrollment date and therefore do not have the ability to judge objective response. Reports generated by LRR may not initially conform to protocol-specific case report forms (CRFs), and the local investigator team typically utilizes the LRR report and translates this information into a CRF per the clinical trial study protocol.

ICR of images is advocated by regulatory authorities as a means of independent verification of clinical trials endpoints dependent on medical imaging. In this context, ICR is the process by which all radiologic exams and selected data acquired as part of a clinical trial study protocol are submitted to a central location and reviewed by independent physician reviewer(s) who are not involved in the treatment of the patients. The independent physician reviewer(s) are blinded to various components of the data, frequently including blinding to treatment arm, patient demographics, assessments made by the investigator, and the results or assessments of other physician reviewers participating in the review process. With ICR, the independent physician reviewer(s) undergo training on the specifics of the study protocol and response criteria, the same physician reviewer(s) follow all patients throughout the study, the same target lesions are followed throughout the study, and the independent physician reviewer(s) fill out the CRF and determine objective response in comparison to the baseline study or lowest tumor burden (nadir). The workflow process is more tightly regulated and standardized with ICR than with LRR. With many phase 2 and 3 studies, ICR is by two primary physician reviewers who independently review each patient's images, and a third adjudicating physician reviewer resolves discordant results when the two primary physician reviewers disagree.

There is frequently discordance among different physician reviewers, resulting in discordance between LRR and ICR and between central physician reviewers participating in ICR. Factors influencing discordance include target lesions selection, inter- and intra-reader differences in target lesion measurement technique, mathematical and data transfer errors, target lesion selection errors, errors in following objective response criteria, workflow differences, limited amount of clinical information, treatment bias, handling of missing data, variability in protocol training, variability in understanding of and application of tumor response criteria, failure to compare to all prior studies, perception of new lesions, subjective assessment of non-target lesions and perception of unequivocal progression of non-target lesions, tumor type, drug efficacy, precision of the response criteria, and complexity of the response criteria.

A critical component of any tumor response criteria is the choice of target lesions on the baseline exam. In clinical practice and clinical trials, the choice of target lesions is at the discretion of the physician reviewer, which could be a radiologist, oncologist, radiation oncologist, surgeon, etc. Most tumor response criteria provide guidance on target lesion selection. For example, RECIST 1.1 provides guidance on which lesions are measurable or non-measurable and then provides additional details on how to select target lesions. In general target lesions and lymph nodes are selected based on their size, though the target lesions must be representative of all involved organs and should lend themselves to reproducible repeated measurements.

The single factor that historically contributes the most to discordance in objective response between physician reviewers is the choice of the target lesions on the baseline scan. In patients with multiple potential target lesions, different physician reviewers will frequently pick different target lesions on the baseline exam. For example, in a patient with multiple potential target lesions in multiple organs, one physician reviewer may select two target lesions in the lungs, two in the liver, and one lymph node while another physician reviewer may pick two different target lesions in the lungs, one in the liver, one in the adrenal, and a different lymph node. Each potential target lesion may grow or regress at a slightly different rate, contributing to different objective responses between physician reviewers that choose different target lesions.

Furthermore, tracking of target lesions over time is advantageous for obtaining accurate and precise objective response. Conventional methods for tracking target lesions include recording target lesions size, organ location, and image number or slice position on CRFs. Some image viewing workstations also keep track of key images. Even with these techniques, local physician reviewers often do not have access to the CRFs or key images of other reviewers, leading to variability in longitudinal tracking of target lesion growth and regression. Similarly, conventional commercial image viewers do not include sophisticated target lesion tracking systems that are readily available when evaluating subsequent time points.

BRIEF SUMMARY

Technical Problem

There is a need for a method and/or system for determining an objective tumor response to an anti-cancer therapy using cross-sectional medical images in such a way that the method and/or system enables standardized target lesion selection and tracking. This technical need is particularly exacerbated when considering phase 2 or 3 industry-sponsored oncologic clinical trials where concordant identification and tracking of target lesions within the same patient can dramatically affect the interpretation of clinical trial endpoints that are dependent on medical imaging. Typical phase 2 or 3 industry-sponsored oncologic clinical trials include a combination of local radiologic review (LRR) and independent central review (ICR). LRR is fraught with touchpoints that are likely to promote discordance. For example, with LRR multiple different local physician reviewers may choose and measure different target lesions without knowledge of the specific response criteria and may select different lesions at different time points. Even within the more controlled ICR, where two primary physician reviewers independently review each patient's images and a third adjudicating physician reviewer resolves discordant results when the two primary physician reviewers disagree, unresolvable discordance remains due to, among other things, inter- and intra-reader differences in target lesion selection in the baseline exam and tracking thereafter. Each potential target lesion may grow or regress at a slightly different rate, contributing to different objective responses between physician reviewers that choose different target lesions.

There are currently no practical methods for different physician reviewers to identify the same target lesions on a baseline exam and longitudinally track them over time. Consequently, there are errors and inconsistencies in clinical trial results, particularly, errors and inconsistencies that can affect the outcomes and conclusions drawn from clinical trials, which may impact clearance and use of potentially life-saving therapeutics.

Technical Solution

Embodiments of the present disclosure include systems, methods, and computer-program products for standardizing target lesion selection within cross-sectional medical images. For example, a computer system can send a plurality of cross-sectional images to a user device for a baseline exam, each cross-sectional image including a cross-sectional slice of digital medical image data captured at a first timepoint from a radiologic device. The computer system can then receive user input (e.g., from the primary reviewer) identifying a set of pixels corresponding to each target lesion selected and generate a target lesion location file that includes a precise anatomical location of each cross-sectional image having an identified target lesion and a pixel location of each target lesion within the cross-sectional images.

The cross-sectional images and target lesion location file can be accessed by subsequent reviewers. When each relevant cross-sectional image is viewed by subsequent reviewers at a computer system (the same computer system as the primary reviewer or a different computer system), the location information for each target lesion is identified from the target lesion location file, and a digital marker is displayed on each target lesion. This allows each reviewer to identify, segment, and otherwise characterize the same target lesions as the primary reviewer at each timepoint. The computer system can additionally use the target lesion location file to identify corresponding cross-sectional images at later timepoints that include previously identified/characterized target lesions and to guide the display of a digital marker on those images that identifies the location of the previously identified/characterized target lesion within the corresponding cross-sectional images.

As another example, embodiments disclosed herein include a method for standardizing target lesion selection within cross-sectional medical images that includes the acts of: (i) receiving a cross-sectional image comprising a cross-sectional slice of digital medical image data captured at a first time point from a radiologic device; (ii) receiving a user input identifying a set of pixels within the cross-sectional image that correspond to a segmented target lesion; (iii) determining one or more target lesion metrics of the segmented target lesion; and (iv) generating a target lesion location file that includes at least a precise anatomical location of the cross-sectional image and a pixel location of the central aspect of the target lesion. The method can additionally include: (v) receiving an authentication request from a second user; (vi) accessing the target lesion location file; (vii) displaying the cross-sectional image to the second user; and (viii) displaying a digital marker at the central aspect of the target lesion on the cross-sectional image. This and similar methods can be executed for a plurality of additional target lesions at additional timepoints.

The disclosed systems and methods can, in some embodiments, enable a reduction of variability in target lesion selection and thereby a reduction in discordant objective response between independent reviewers. In some instances, the disclosed embodiments can be additionally beneficial to adjudication, whereby an adjudicator can review target lesion selection and measurements from more than one primary and/or secondary reviewer.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF FIGURES

In order to describe the manner in which the above recited and other advantages and features of the invention can be obtained, a more particular description of the invention briefly described above will be rendered by references to specific embodiments thereof, which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION

Figure 1:
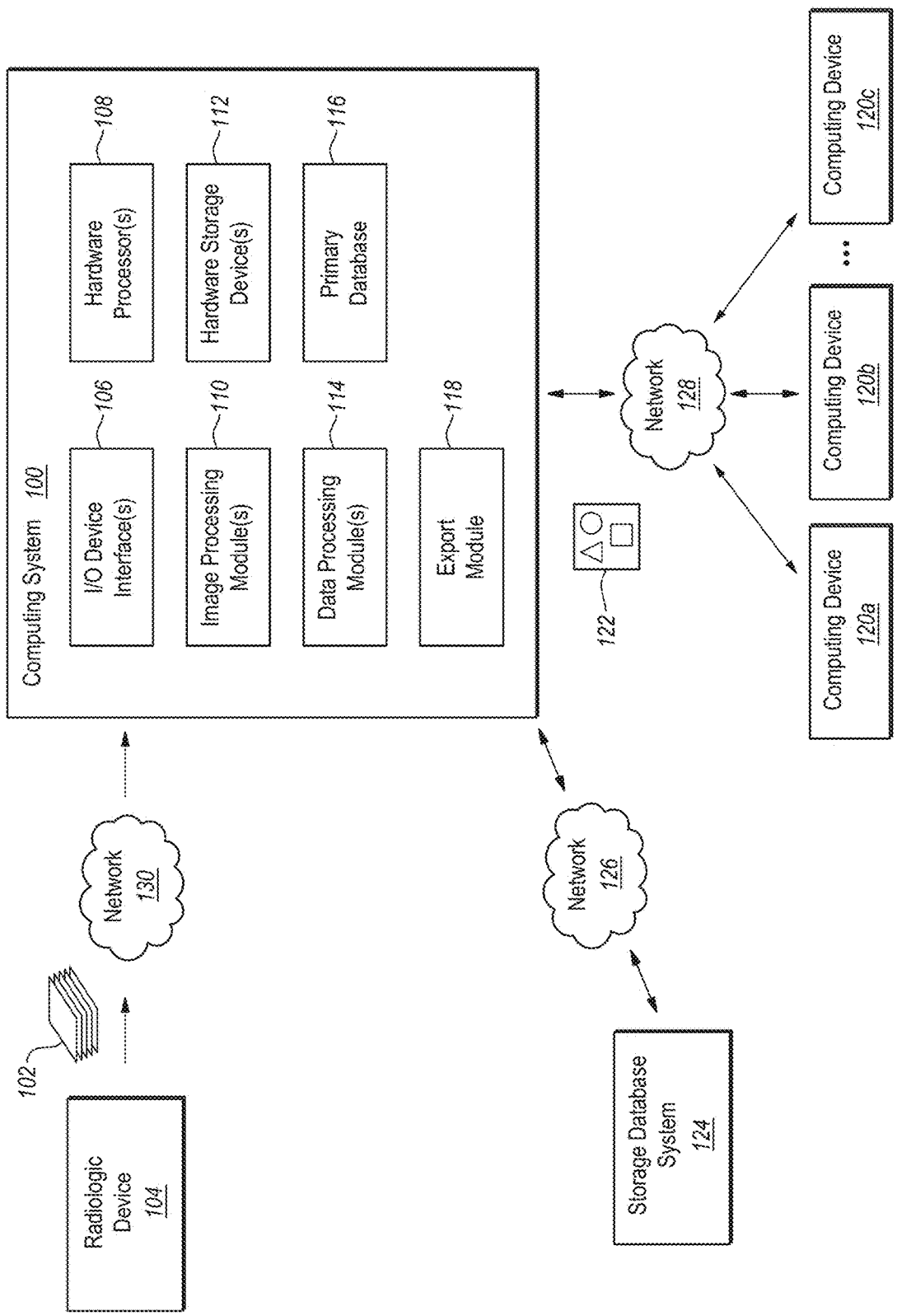
FIG. 1 is a schematic representation of a system for determining an objective tumor response to an anti-cancer therapy using one or more cross-sectional images according to one or more embodiments of the present disclosure.

While the detailed description is separated into sections, the section headers and contents within each section are not intended to be self-contained descriptions and embodiments. Rather, the contents of each section within the detailed description are intended to be read and understood as a collective whole where elements of one section may pertain to and/or inform other sections. Accordingly, embodiments specifically disclosed within one section may also relate to and/or serve as additional and/or alternative embodiments in another section having the same and/or similar systems, modules, devices, methods, and/or terminology.

The embodiments disclosed herein will now be described by reference to some more detailed embodiments, with occasional reference to any applicable accompanying drawings. These embodiments may, however, be embodied in different forms and should not be construed as limited to the embodiments set forth herein. Rather, these embodiments are provided so that this disclosure will be thorough and complete, and will fully convey the scope of the embodiments to those skilled in the art.

As alluded to above, it is often necessary in clinical trials to evaluate patients by a variety of imaging-based tumor response criteria. As each criterion has different standards and methods for target lesion selection, it is quite challenging to minimize errors both within and between reviewers when evaluating patients using one or more of the known imaging-based tumor response criteria. This challenge is exacerbated when physician reviewers are identifying and evaluating different target lesions within the same patient, as it frequently results in discordance among the reviewers.

A critical component of any tumor response criteria is the choice of target lesions on the baseline exam. In clinical practice and clinical trials, the choice of target lesions is at the discretion of the physician reviewer. Most tumor response criteria provide guidance on target lesion selection, and in general target lesions and lymph nodes are selected based on their size, though the target lesions must be representative of all involved organs and should lend themselves to reproducible repeated measurements. However, in patients with multiple potential target lesions, different physician reviewers will frequently pick different target lesions on the baseline exam. Each potential target lesion may grow or regress at a slightly different rate, contributing to different objective responses between physician reviewers that choose different target lesions.

Embodiments of the present disclosure enable the identification and tracking of target lesions throughout a clinical trial or treatment regimen so that one or more secondary reviewers can rapidly access key images that include target lesions identified by the primary reviewer at the baseline scan. In some aspects of the disclosed embodiments, the target lesions are identified on each key image by a digital marker that indicates a central aspect of the target lesion or otherwise indicates the general area of the cross-sectional image where the target lesion is located. Using the digital marker as a guide, the secondary reviewers can identify the corresponding target lesion within the cross-sectional image and conduct their own segmentation, measurements, and review of the target lesion.

The methods and systems of the present disclosure are useful for evaluating tumor response to chemotherapy, targeted therapy, immunotherapy, radiation therapy, surgical therapy, ablative therapy, hyperthermia therapy, photodynamic therapy, laser therapy, gene therapy, biologic vector therapy, artificial vector therapy, and other forms of therapy. Further, the methods and systems of the present disclosure are applicable and useful to evaluate primary tumors, locoregional spread of tumors, and metastatic tumors; benign and malignant tumors; and a variety of tumor types, including: skin cancer, lung cancer, prostate cancer, breast cancer, colorectal cancer, kidney cancer, lymphoma, thyroid cancer, brain cancer, bone cancer, connective tissue cancer, muscle cancer, liver cancer, gastrointestinal cancer, pancreatic cancer, esophageal cancer, stomach cancer, melanoma, gynecologic cancer, cardiac cancer, etc.

As described in greater detail below, the digital markers used in many of the disclosed embodiments identify a target lesion within a given cross-sectional image in such a way that the physician reviewer can identify which lesion within the cross-sectional image is the target lesion of interest without biasing the physician reviewer's segmentation of the target lesion or the corresponding measurements related thereto. For example, a digital marker can be displayed over a central aspect of the target lesion, as calculated from the primary reviewer's segmented target lesion, without detailing the exact boundary of the target lesion. One or more secondary reviewers are then free to segment and measure the target lesion in accordance with their own professional judgment. In this way, discordance resulting from a lack of standardized target lesion selection and tracking can be reduced or eliminated, thereby providing greater clarity into the efficacy of potential therapeutics.

Systems for Determining Objective Tumor Response

Referring now to FIG. 1, depicted is a schematic representation of a system for determining an objective tumor response to an anti-cancer therapy using one or more cross-sectional images, which can serve as the basis for one or more embodiments of the present disclosure. FIG. 1, generally, includes a computing system 100 configured to determine an objective tumor response. The computing system 100 may receive one or more cross-sectional images 102 from a radiologic device 104. The radiologic device 104 and the computing system 100 can be physically connected such that the one or more cross-sectional images 102 are transferred via the physical connection. Alternatively, the computing system 100 can receive the cross-sectional images 102 from the radiologic device 104 via a network 130 digitally connecting the radiologic device to the computing system 100, as known in the art. The network 130 may be a private network, such as an intranet of a hospital, or the network 130 may be a public network such as the Internet.

The radiologic device 104 illustrated in FIG. 1 can include any medical imaging device that generates cross-sectional images obtained by at least one of: x-ray computed tomography (CT), computed tomography perfusion (CTP) imaging, positron emission tomography (PET), single-photon emission computed tomography (SPECT), magnetic resonance imaging (MRI), or ultrasound. Consequently, the cross-sectional images include digital medical image data in the form of: CT images, CTP images, PET images, SPECT images, MRI images, or ultrasound images, respectively.

Upon receiving the cross-sectional images 102, the computing system 100 may store the cross-sectional images 102 in a primary database 116 or a hardware storage device 112 for later access or may process one or more of the cross-sectional images 102. By processing any of the cross-sectional images 102, the computing system 100 identifies target lesions within the cross-sectional images 102. The target lesions are identified according to requirements disclosed by pre-defined tumor response criteria stored within computing system 100 or accessed through network 130. In some embodiments, the pre-defined tumor response criteria may be user-defined, or it may be defaulted to a particular tumor response criterion such as, for example, the RECIST 1.1 Criteria. In yet other embodiments, the computing system 100 determines which tumor response criteria to use based on data within the cross-sectional images 102, such as, for example, the anatomical location represented in the cross-sectional images 102 or by the presence or absence of injected radiocontrast in the cross-sectional images 102.

Upon identifying the target lesions from the cross-sectional images 102, the user or the computing system can select a particular slice for each of the target lesions. The slice may be selected by, for example, determining the slice from the cross-sectional images 102 where the given lesion has the longest length measurement. Other lesion characteristics may be used in selecting the slice, including, for example, the length of the short axis or the area of the lesion or the slice with the largest amount of vascular tumor. Selecting a particular slice for each of the target lesions may be carried out by an image processing module 110 of the computing system 100 and may be done automatically, or it may be selected by a user through an I/O device interface 106.

The computing system 100 can analyze a target lesion with an image processing module 110 by performing any of the following: identify a total range of pixel intensities within the target lesion; restrict the total range of pixel intensities to a first restricted range of pixel intensities, wherein the first restricted range of pixel intensities corresponds to a first subset of pixel intensities representative of vascularized tumor; and determine one or more lesion metrics. In some embodiments, the image processing module 110 is specifically configured to identify a total range of pixel intensities within the target lesion and restrict the total range of pixel intensities to a first restricted range of pixel intensities.

In any of the foregoing embodiments where the image processing module 110 is configured to restrict the range of pixel intensities, the restricted range of pixel intensities may be set to any range of pixel intensities automatically determined by the computing system 100 or as directed by the user through I/O device interface 106. Additionally, or alternatively, the restricted range of pixel intensities may be informed by a selected tumor response criterion. The image processing module 110 or other components of the computing system 100 can compensate for the presence or absence of injected radiocontrast, as necessary. Such compensation, and other functionalities of computer system 100, can be performed as described in U.S. Pat. No. 9,826,951, which is incorporated herein by reference in its entirety.

For example, the image processing module 110 or a user can determine lesion metrics from selected target lesions. The lesion metrics can be determined by a user at a user interface, such as the I/O user interface 106 of computing system 100, and the image processing module 110 can calculate and/or determine the user-specified lesion metrics for the target lesions. Lesion metrics may include a longest dimension length, a short axis dimension length, a longest dimension length of vascularized tumor, a pixel area of the at least one of the one or more target lesions, a pixel area within the first restricted range, a pixel area within the second restricted range, a mean value of pixel intensities within the total range of pixel intensities, a mean value of pixel intensities within the first restricted range of pixel intensities, a histogram parameter that includes a quantitative distribution of pixel intensities in the target lesion, or a texture parameter that includes a geographic distribution of pixel intensities in the target lesion.

Importantly, determining the objective tumor response and any of the other disclosed derivations, determinations, or analyses performed in embodiments incorporating aspects of the computing system 100 of FIG. 1 may be done automatically by the computing system, may be performed after receiving one or more user instructions at a computer interface, or may be performed as a combination thereof. In some embodiments, the computing system acts as a guide for the user, leading the user to determining an objective tumor response from one or more cross-sectional images and preventing errors in target lesion selection (according to the selected tumor response criteria or by way of directing subsequent users to evaluate the same target lesions as the primary reviewer), data transfer, mathematical processing, response classification, and data and image archival. In other embodiments, the computing system automatically computes and derives data such as the objective tumor response. The computing system may automatically calculate or determine a plurality of tumor response criteria and may selectively, reiteratively, or automatically calculate any lesion metrics, tumor response criteria, or other data in response to a user editing or changing one or more criteria at a user interface.

While FIG. 1 depicts several independent modules 106, 108, 110, 114, 116, 118, one will understand the characterization of a module is at least somewhat arbitrary. In at least one implementation, the modules 106, 108, 110, 114, 116, 118 of FIG. 1 may be combined, divided, or excluded in configurations other than that which is shown. As used herein, the individual modules 106, 108, 110, 114, 116, 118 are provided for the sake of clarity and explanation and are not intended to be limiting.

The computing system 100 of FIG. 1 allows for distinct advantages, some of which include reducing the likelihood of human error, increasing reproducibility, and providing a quantitative measure of the pixel intensities for target lesions as required under certain tumor response criteria, which would otherwise be left to subjective guesswork. Further, the computer system 100 of FIG. 1 allows for simultaneous measurement of a plurality of tumor metrics, simultaneous assessment of lesions by multiple tumor response criteria, reduced read times, automated mathematical calculations of summary data, automated generation of key images, automated archiving of regions of interest data, automated archiving of tumor metric data, and instant generation of a summary report.

The latter two elements will now be discussed with continued reference to FIG. 1. Data determined, derived, and/or analyzed at computing system 100 may be exported by export module 118 and archived in a storage database system 124, which can include persistent memory. The storage database system 124 may be remote from the computing system such that the computing system transfers the data to be archived at storage database 124 over a network 126. The network 126 may be the same network as networks 128 and 130 but, in some embodiments, it may be a different network.

The computing system 100 may export and store a target lesion location file 122 locally within one of the hardware storage device(s) 112, or it may export and store the target lesion location file in external persistent memory, such as within storage database 124. The target lesion location file 122 can include the precise anatomical location of the target lesion and/or cross-sectional image containing the target lesion (e.g., the three-dimensional location within the user's body where the cross-sectional image containing target lesions was captured), target lesion metrics (including, for example, segmentation date for the target lesion), and/or a location within the cross-sectional image where the digital marker is to be displayed to visually indicate an area where the target lesion was previously identified by the primary reviewer. In some embodiments, the target lesion location file 122 is generated at a user computing device (e.g., computing devices 120a, 120b, 120c) and transferred to the computing system 100 or storage database system 124 for storage and later access. In some embodiments, a single target lesion location file 122 may be used. In other embodiments, multiple target lesions location files may be used. Each target lesion may have a separate target lesion location file. Each user may have a separate target lesion location file. Each instance may have a separate target lesion location file.

A target lesion location file may be modified or replaced with a new target lesion location file. In some implementations, there is a master target lesion location file, whether remotely or locally stored at one or more computing systems.

In some embodiments, the cross-sectional images and target lesion location files are shared via a local computer hard drive, a portable storage device, through an electronic correspondence, through a wired digital file transfer and storage method, through a wireless digital file transfer and storage system, through a distributed and/or cloud-based file transfer and storage system, or through a web-based file transfer and storage system, as known in the art.

It will be appreciated that the computing devices 120a, 120b, 120c can have any or all of the components and modules described above for the general computing system 100. In some instances, the computing system 100 can include the work station of a primary reviewer. Alternatively, the computing system 100 can include a server for hosting or facilitating user interaction with cross-sectional images and/or computer-executable instructions (e.g., in the form of software or a SaaS platform) for standardizing target lesion identification and selection within cross-sectional images, as described herein. Similarly, the computing devices 120a, 120b, 120c can represent the work stations of secondary reviewers or an adjudicating reviewer, or the computing devices 120a, 120b, 120c can be user profiles or virtual instances of computing system 100.

Regardless of the physical and virtual organization of the computing system 100 and the associated computing devices 120a, 120b, 120c, embodiments of the present disclosure enable cross-sectional images to be received and/or viewed at any of the foregoing system/devices 100, 120a, 120b, 120c and to be further informed by a target lesion location file 122 for the standardization of target lesion selection and evaluation between primary and secondary reviewers. For example, whether accessed locally or remotely, a secondary reviewer can be brought to a first target lesion (which may be identified by a digital marker) and prompted to measure and/or segment the target lesion contained therein, and upon entering measurements and/or segmentation data, the secondary reviewer can be automatically taken to (or prompted to progress to) a next cross-sectional image where a subsequent target lesion is measured and/or segmented. This process can be continued until all (or a plurality) of the target lesions are measured and/or segmented by the secondary reviewer.

Embodiments of the present disclosure additionally provide for the generation of a summary image following target lesion identification by the physician reviewer. For the ease of illustration, the disclosed concept of standardizing target lesion selection and analysis thereof will be discussed within the context of summary images. However, it should be appreciated that the disclosed methods for standardizing target lesion selection and analysis can be applied within other workflows to generate a different summary analysis. For example, the cross-sectional images can be presented, themselves, instead of a stack of segmented target lesions taken therefrom and can be accompanied by a summary or listing of target lesion metrics with or without an indication of objective tumor response. With this understanding, applications of the disclosed systems and methods for standardizing target lesion selection and analysis will be elaborated in FIGS. 2-6 within the context of summary images.

Figure 2:
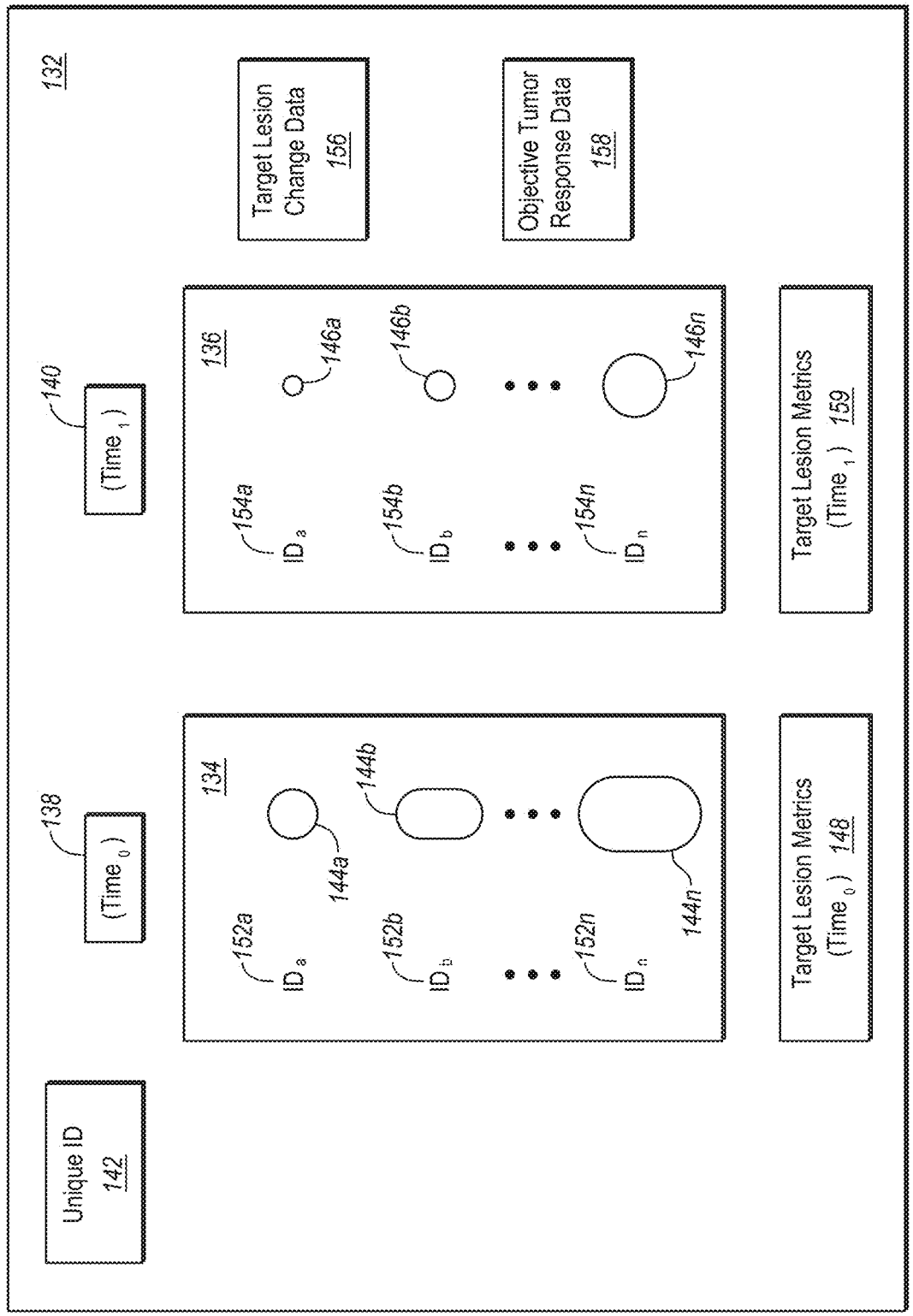
FIG. 2 is a schematic representation of a computer interface depicting a customizable summary image of target lesions selected by a single reviewer and tracked between two exemplary timepoints in accordance with an embodiment of the present disclosure.

For example, FIG. 2 illustrates a computer interface comprising a customizable summary image 132. The customizable summary image 132 includes a first illustration 134 of target lesions 144a, 144b, 144n taken at a first point in time 138 (e.g., a baseline measurement) and a second illustration 136 of target lesions 146a, 146b, 146n taken at a second or subsequent point in time 140. The target lesions 146a, 146b, 146n in the second illustration 136 can represent the target lesions 144a, 144b, 144n displayed in the first illustration 134 following treatment. Each target lesion 144a, 144b, 144n, 146a, 146b, 146n can be associated with a label 152a, 152b, 152n, 154a, 154b, 154n, which can identify the location of the target lesion (e.g., lymph node, lung, liver, etc.) or any other identifying characteristic of the target lesion. In some embodiments, the labels 152a, 152b, 152n associated with target lesions 144a, 144b, 144n in the first illustration 134 can be the same labels 154a, 154b, 154n associated with target lesions 146a, 146b, 146n in the second illustration 136.

As depicted, there are at least three target lesions 144a, 144b, 144n, where n is an integer greater than 2. Though depicted as at least three target lesions, it will be appreciated that the first illustration 134 may depict as few as one target lesion and that the number of target lesions in the second illustration 136 may be greater or less than the target lesions in the first illustration. For example, if new metastases arise between the first and second point of time 138, 140, there may be a greater number of target lesions in the second illustration 136 than in the first 134. If, however, the anti-cancer therapy is working, there may be two time points in the monitored therapy wherein the second illustration 136 has fewer target lesions as compared to the first illustration 134 due to a significant reduction in size of the tumor and/or destruction of the tumor.

In addition to the first and second illustrations 134, 136, the customizable summary image 132 further includes target lesion metrics (Time$_0$) 148, target lesion metrics (Time$_1$) 159, target lesion change data 156, and object tumor response data 158. The customizable summary image 132 may also contain a unique ID 142, which may include patient identification information such as the patient's name, medical record number, date of birth, a coded identification number, or an anonymous patient ID number.

On the other hand, other embodiments of the present disclosure provide that the determination of which component(s) of the foregoing additional components will be displayed with the first illustration and the second illustration in the customizable summary image 132 is dependent upon one or more user selections at a user interface and/or at I/O device 106 of the computing system 100. The user may, in some embodiments, select one or two components, a plurality of components, or all of the components to be displayed with the first illustration and the second illustration in the customizable summary image 132.

Figure 3:
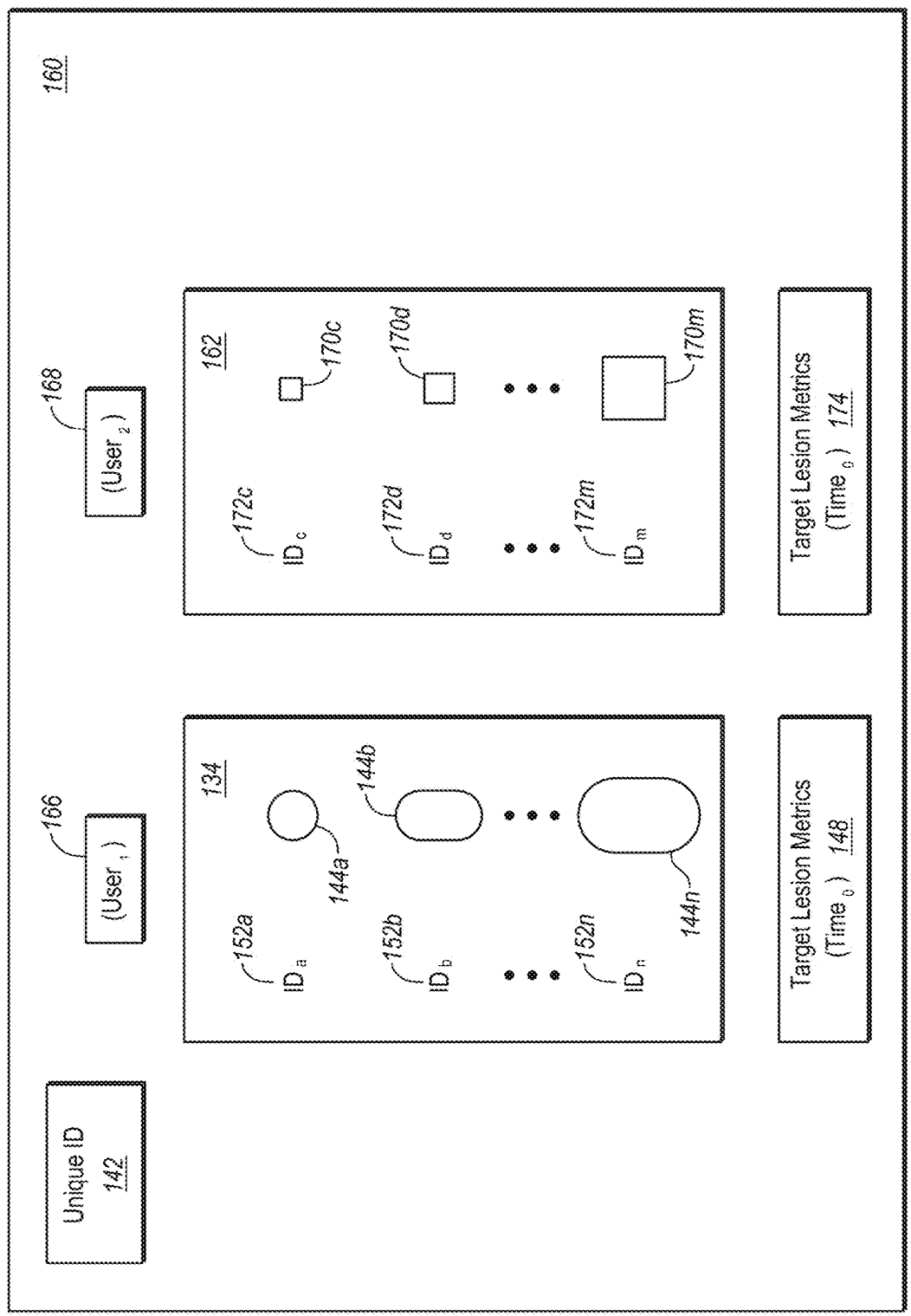
FIG. 3 is a schematic representation of a computer interface depicting a customizable summary image of target lesions selected by different reviewers at an exemplary timepoint in accordance with an embodiment of the present disclosure.

The customizable summary image 132 illustrated in FIG. 1 can be exemplary of the results of a single physician reviewer identifying and tracking target lesions within a patient who is undergoing anti-cancer therapy. The single physician reviewer can track the same target lesions throughout time to determine an objective tumor response. However, as shown in FIG. 3, it is often the case that a secondary reviewer 168 (e.g., User$_2$) selects one or more different target lesions 170c, 170d, 170m than the primary reviewer 166 (e.g., User$_1$). This results in substantially different target lesion metrics 174 than those target lesion metrics 148 calculated for the target lesions 144a, 144b, 144n identified by the primary reviewer 166.

Figure 4:
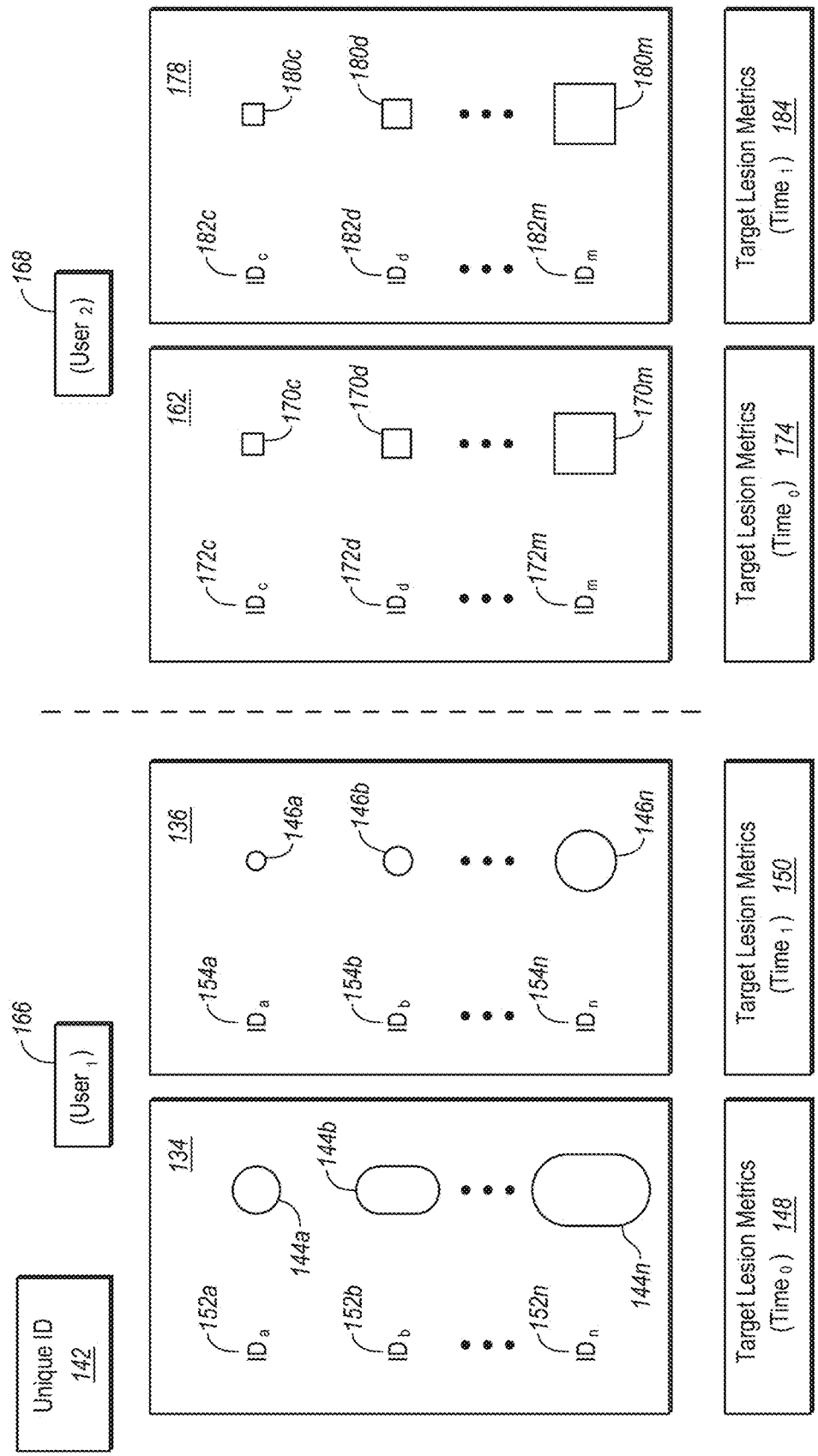
FIG. 4 is a schematic representation of a computer interface depicting a customizable summary images of target lesions selected by different reviewers and tracked between two exemplary timepoints in accordance with an embodiment of the present disclosure.

Accordingly, as shown in FIG. 4, when comparing a time lapse of target lesion analysis between a primary reviewer 166 and a secondary reviewer 168, the target lesions 144a, 144b 144n, 146a, 146b 146n identified and associated target lesion metrics 148, 150 calculated by the primary reviewer 166 can be substantially different than the target lesions 170c, 170d, 170m, 180c, 180d, 180m identified and associated target lesion metrics 174, 184 calculated by the secondary reviewer. This can lead to discordance in the determination of an objective tumor response for target lesions obtained from the same patient or set of cross-sectional images associated with the same unique ID 142.

Figure 5:
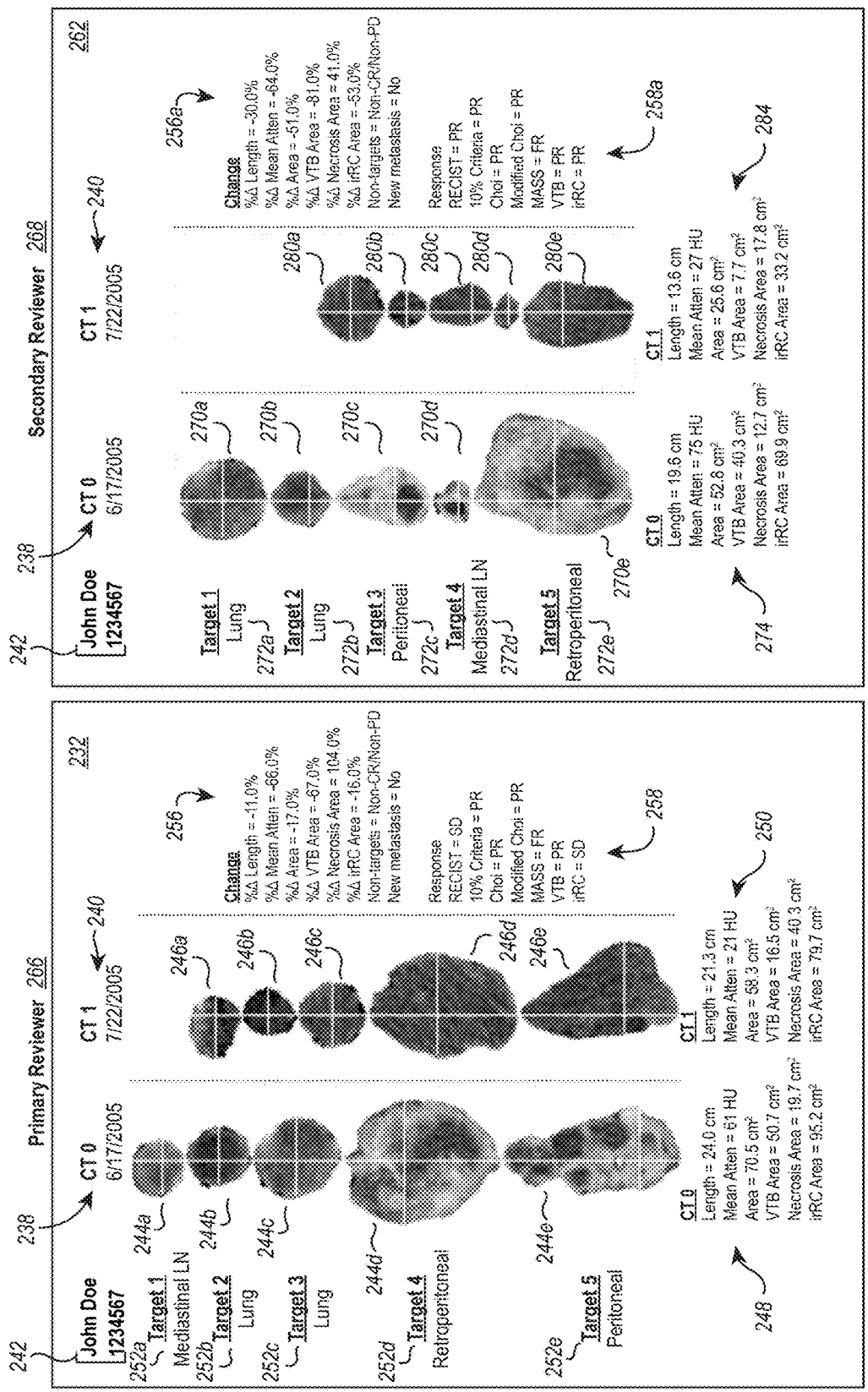
FIG. 5 illustrates summary images of target lesions selected by a primary reviewer (left) and a secondary reviewer (right) as an exemplary instance of reviewers choosing different target lesions on the baseline exam—without a method for tracking target lesion selection—that ultimately lead to discordant objective tumor response results.

A specific example of this is illustrated in FIG. 5, where a primary reviewer 266 identified five different target lesions 244a, 244b, 244c, 244d, 244e at a first time point 238 (CT0) and tracked the same target lesions to a second point in time 240 (CT1). The target lesions 246a, 246b, 246c, 246d, 246e tracked to the second point in time 240 (CT1) are reduced in size—as indicated by the reduced stack size and by the summary of the target lesion change data 256 derived from the target lesion metrics 248, 250 at each time point. An objective tumor response 258 was calculated and/or determined by the primary reviewer 266 based on the target lesion metrics 248, 258 and change data 256.

A secondary reviewer 262 identified five target lesions 270a, 270b, 270c, 270d, 270e at the first time point 238 (CT0) and tracked these target lesions to the second point in time 240 (CT1) where these target lesions 280a, 280b, 280c, 280d, 280e also demonstrated a reduction in size—as indicated by the reduced stack size and by the summary of the target lesion change data 256a derived from the target lesion metrics 274, 284 at each time point. An objective tumor response 258a was similarly calculated and/or determined by the secondary reviewer 268 based on the target lesion metrics 274, 284 and change data 256a.

As can be seen by comparison of the objective tumor responses 258, 258a determined by the primary 266 and secondary 268 reviewers, there is discordance as to the objective tumor response within a subset of the tumor response criteria. Such a result is a common problem in the art—one that embodiments of the present disclosure address.

With further analysis of FIG. 5, it can be seen that the secondary reviewer 268 selected some of the same target lesions as the primary reviewer 266. For example, the first target lesion 270a selected by the secondary reviewer 268 includes an identifier 272a that indicates the target lesion 270a was taken from a cross-sectional image of the lung. This target lesion 270a matches the third target lesion 244c identified by the primary reviewer 266. Additionally, the retroperitoneal target lesion 270e identified by the secondary reviewer 268 is the same retroperitoneal target lesion 244d identified by the primary reviewer 266. While the first reviewer 266 and second reviewer 268 each also identified target lesions from peritoneal, mediastinal lymph node, and lung cross-sectional images, the target lesions selected at each of these additional locations were different. This results in different target lesion metrics 248, 250, 274, 284 (e.g., different mean attenuation, different lengths, different areas, etc.) at and between the first and second timepoints 238, 240, and because the target lesion metrics serve as a basis for calculating the objective tumor responses 258, 258a, discordance arises. Such results make it difficult to determine whether, or to what degree, a therapy is working.

By standardizing target lesion selection at the baseline measurement, each subsequent reviewer segments and analyzes the same target lesions, reducing the discordance between reviewers that results from target lesion selection. In certain embodiments, the target lesions are manually segmented using a free-form region of interest tool. In other embodiments, the target lesions are segmented using pixel thresholding techniques or automated target lesion detection methods.

In some embodiments, the target lesions are automatically segmented by the computer system prior to viewing and analysis by the primary reviewer. In other embodiments, the reviewer first confirms location of the digital markers and target lesions and then image segmentation occurs on a manual, semi-automated, or fully automated basis. In still other embodiments, the computer system automates some but not all the target lesion localization and image segmentation, a reviewer assists with or corrects any incomplete or incorrect target lesion localization or image segmentation.

Figure 6:
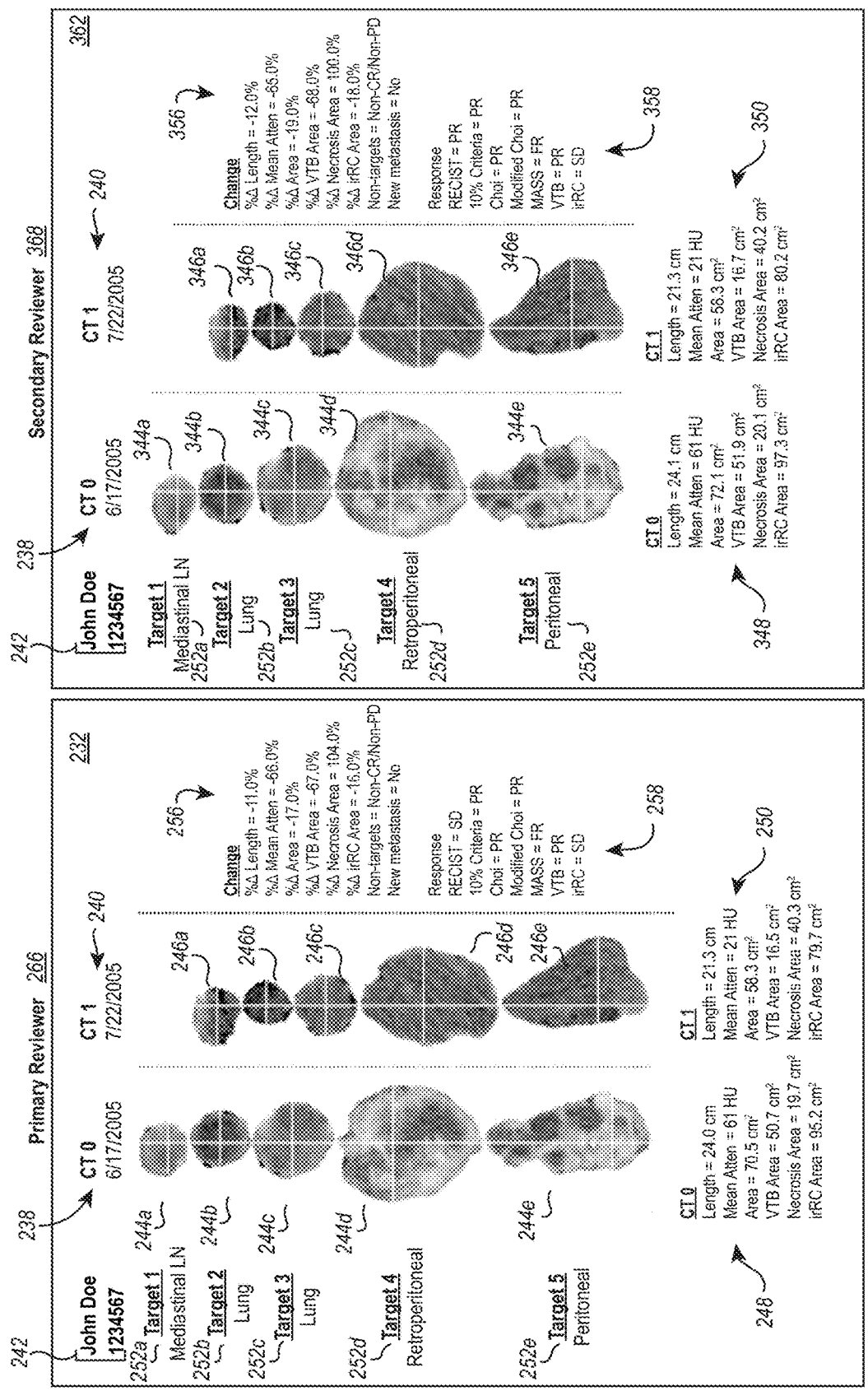
FIG. 6 illustrates summary images of target lesions selected by a primary reviewer (left) and a secondary reviewer (right) as an exemplary instance of reviewers using a computer-assisted method for standardizing target lesion selection and tracking on medical images, thereby leading to concordant objective tumor response results.

FIG. 6 illustrates summary images of target lesions selected by a primary reviewer (left) and a secondary reviewer (right) as an exemplary instance of reviewers using the disclosed methods for standardizing target lesion selection and tracking on medical images to increase concordant objective tumor response results. As can be see in FIG. 6, a summary image 232 of the target lesions selected by the primary reviewer 266, along with the associated target lesion metrics and objective tumor response, are the same as those shown in FIG. 5. However, instead of the secondary reviewer 268 of FIG. 5 identifying their own set of target lesions for analysis and tracking, the secondary reviewer 368 of FIG. 6 was provided with cross-sectional images that included the target lesions identified by the primary reviewer 266 and was able to subsequently segment and measure the same target lesions as the primary reviewer 266.

Because target lesion segmentation can include a measure of professional interpretation and discretion, the target lesions 344a, 344b, 344c, 344d, 344e identified by the secondary reviewer 368, while the same lesions within the same cross-sectional images as those identified by the primary reviewer 266, have a slightly different shape and corresponding target lesion metrics (as seen, for example, in the comparison of target lesion metrics 248 and 348). Thus, embodiments of the present disclosure enable the evaluation of anti-cancer therapies more consistently and based on the variance in professional interpretation of medical images, rather on the random selection of target lesions. Even if target lesion selection is somewhat guided by tumor response criteria, different target lesions can be chosen by different physician reviewers (as illustrated in FIG. 5), which can spawn unnecessary variability into the determination of whether or not anti-cancer therapies are effective, particularly within clinical trial settings.

In one embodiment, the primary reviewer selects a set of target lesions for a baseline measurement. The anatomical location of each target lesion (e.g., lung, lymph node, peritoneal, etc.) is stored within a target lesion location file along with an identifier for the cross-sectional image used by the primary reviewer for each target lesion. In some instances, the target lesion location file additionally includes target lesion metrics for each target lesion or other data that can be used to indicate a location of the target lesion within the cross-sectional image. For example, the target lesion location file can include a pixel location of the central aspect of the target lesion, as the central aspect is defined by the primary reviewer's segmentation of the target lesion.

In certain embodiments, the computer system identifies the central aspect of each target lesion. This can be accomplished in a variety of ways. For example, the center of a length measurement, either the longest dimension or short axis, can serve as the center of the target lesion. If a freeform region of interest is drawn by the physician reviewer, the longest dimension or short axis length can be derived, and the center of the line for the longest dimension or short axis length can serve as the center of the target lesion.

It should be appreciated that the computer system can identify the central aspect of each target lesion in a variety of additional, or alternative, ways. For example, the computer system can identify the central aspect of each target lesion by identifying a pixel intensity for each or a plurality of pixels that define a target lesion, and based on the pixel intensities, define a region within the target lesion that includes a highest average intensity. The region of highest average pixel intensity can be selected as the central aspect of the target lesion or a center of the region can be defined as the central aspect of the target lesion. In some embodiments, the center of the region can be selected using any of the methods disclosed herein for selecting a central aspect (e.g., the center of a length measurement of a shortest or longest axis, the cross-section of the shortest and longest axis, etc.).

As an additional example, a line or a plurality of lines can be formed that comprise a continuous line of adjacent pixels spanning from a first side of the target lesion to an opposite side of the target lesion. An average or center of the line or plurality of lines can be used to define the central aspect of each target lesion.

As an additional example, a heat map can be generated from the pixel intensities and a central aspect chosen based on an area comprising a highest intensity as derived from the heat map. In some embodiments, a central aspect is chosen based on a location within the target lesion that represents the average pixel intensity of all or a plurality of pixel intensities within the target lesion.

It should be appreciated that in some embodiments, the central aspect is disposed at a location outside the target lesion (e.g., the central aspect defined by a midpoint along a longest axis of a crescent-shaped target lesion). In such embodiments, the central aspect is maintained at the location outside the target lesion. In other embodiments, the central aspect comprises a location within the target lesion that is proximate or closest to the point or region that was determined to be a central aspect, but which lies outside the target lesion.

It should be appreciated that the target lesions could be marked or annotated in one or more locations using a variety of digital markers. For example, one or more arrows could point to one or more edges of the target lesion. A box or circle could be placed around the target lesion to indicate the location of the target lesion.

Figure 7:
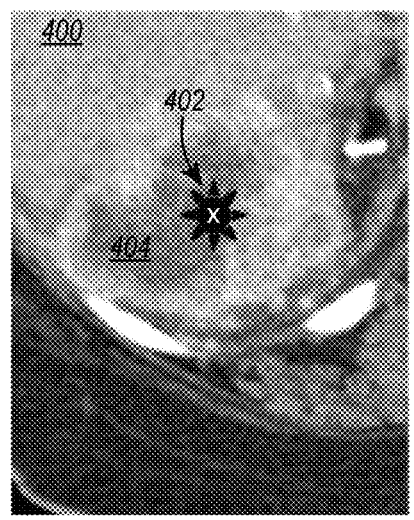
FIG. 7 illustrates an exemplary display of a cross-sectional medical image with a digital marker displayed thereon at or near the corresponding central aspect of a target lesion previously identified by a primary reviewer such that each subsequent reviewer can independently assess the target lesion without being biased by the measurements and/or segmentation from the primary/previous reader.

Data from the target lesion location file can be used to inform the placement of digital markers on cross-sectional images that include target lesions so that subsequent reviewers can easily identify which lesion on the cross-sectional image is to be segmented and measured. For example, as shown in FIG. 7, a cross-sectional image 400 that includes a target lesion 404 previously identified by the primary reviewer. The target lesion 404 is identified by a digital marker 402, the center of which his placed on the central aspect of the target lesion 404. The digital marker 402 allows the secondary reviewer to easily identify the target lesion within the cross-sectional image 400. The secondary reviewer is then free to segment the marked target lesion and make measurements, as necessary.

In one embodiment, the digital marker 402 is displayed over the target lesion until the physician reviewer activates a region of interest/segmentation tool, whereupon the digital marker disappears. This can be advantageous if the digital maker obscures part or all of the target lesion where it would be difficult to accurately segment the target lesion with the digital marker concomitantly displayed. Alternatively, display of the digital marker can be toggled on/off at the user's request.

It should be appreciated that although the digital maker 402 of FIG. 7 includes a letter "X" in the center of an 8-point star, other digital markers can be used. For example, the letter "X" can be replaced with a number indicating which target lesion the digital marker is associated with (e.g., 1 for target lesion 1, 2 for target lesion 2, etc.) or a letter, series of letters, or other symbol indicating the anatomical location of the target lesion and/or whether the target lesion is a metastasis, lymph node, or new lesion. The foregoing can be used alone or in combination with the 8-pointed star shown in FIG. 7. Alternatively, the 8-pointed star can be replaced by any other star or shape that can act as a visual indication of the target lesion location within the cross-sectional image.

In some embodiments, the digital marker can be stored as a pixel or metadata associated with a pixel and can be displayed as a colored, opaque, or partially transparent image or shape displayed at or near the pixel or region of pixels defining the central aspect. A wide variety of colors or shapes could be used. A numbering system could also be used to signify the target lesion number (e.g., in a sequence of target lesions to be measured by a second or subsequent reviewer or which have been measured and/or segmented by a primary reviewer). A combination of colors, various transparencies, and/or a numbering system could also be used. In some embodiments, the numbering system represents the same order of target lesions selected by a primary reviewer. In some embodiments, the order of target lesions is randomized for one or more subsequent reviewers.

In some embodiments, the digital marker 402 is associated with the central aspect of the target lesion 404, as shown in FIG. 7. Alternatively, the digital marker can be positioned along any point of the long or short axes, along any point of the boundary of the target lesion, or it can be a general indication of the area encompassing the target lesion (e.g., an arrow pointing to the target lesion). The digital marker can also be placed on or near the target lesion in accordance with any of the target lesion metrics associated therewith. In a preferred embodiment, the digital marker is placed on the cross-sectional image at any location that unambiguously indicates the target lesion within the cross-sectional image.

Figure 8:
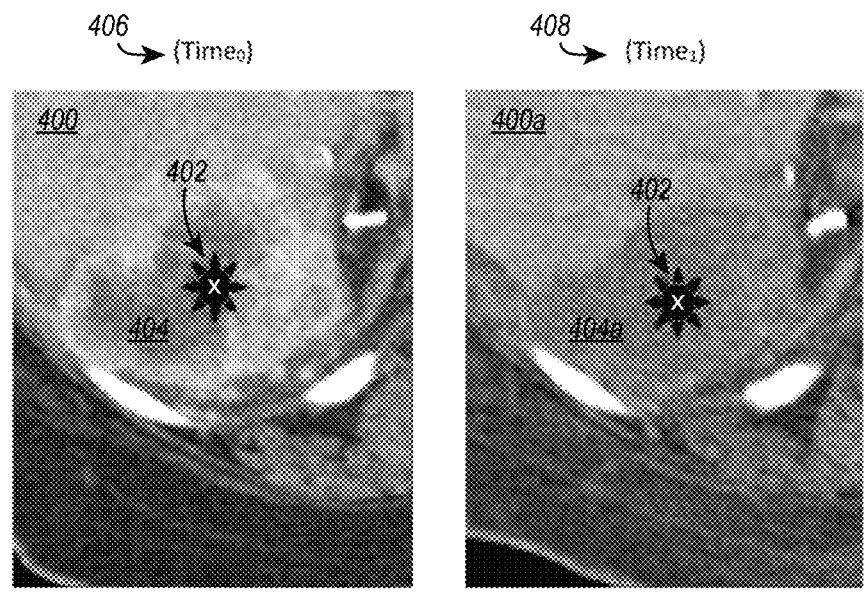
FIG. 8 illustrates an exemplary display of cross-sectional medical images from a baseline exam (left) and a subsequent time point (right) with a digital marker displayed thereon at or near the corresponding central aspect of a target lesion previously identified by a primary reviewer such that each subsequent reviewer can independently assess the target lesion without being biased by the measurements and/or segmentation from the primary/previous reader.

As shown in FIG. 8, the digital marker can additionally be used to indicate the location of a target lesion within a cross-sectional image at different timepoints. Subsequent to the segmentation of the target lesion by the primary reviewer from cross-sectional images captured at a first timepoint (Time$_0$) 406, the location of a digital marker within the cross-sectional image can be determined and saved within a corresponding target lesion location file. A secondary reviewer can access the cross-sectional images or authenticate a request to access the cross-sectional images, whereupon the cross-sectional images are viewed by the secondary user with the digital marker identifying the location of the primary reviewer's selected target lesions. In one embodiment, the secondary reviewer is presented with only those cross-sectional images that include a target lesion, and the target lesions are identified on the cross-sectional images via a digital marker.

In another embodiment, the secondary reviewer is provided with all of the cross-sectional images, and a digital marker is placed on or near the location of the target lesion selected by the primary reviewer (e.g., on the same cross-sectional image associated with the target lesion). The secondary reviewer can contest the target lesion selection (e.g., as not conforming to a selected tumor response criterion or as not being representative) and select additional or other target lesions, or the user can use the cross-sectional images to provide better context into the target lesion selection of the primary reviewer.

As also shown in FIG. 8, the digital marker 402 can additionally be used to identify the target lesion 404a at a second timepoint (Time$_1$) 408. The digital marker 402 can be placed on an analogous cross-sectional image 400a at the same pixel location as determined at the first timepoint (Time$_0$). The analogous image 400a can be identified by the primary reviewer, and the target lesion location file updated with the cross-sectional image 400a location information. Additionally, or alternatively, the target lesion location file can be used to identify the precise anatomical location of the target lesion 404 at the first timepoint 406, and an analogous cross-sectional image 400a can be selected from a set of cross-sectional images captured at the second timepoint that includes the target lesion 404a. The digital marker can be placed at the same (or analogous) pixel location determined at the first time point 406. This can be done, for example, for the primary reviewer (or the first reviewer in time to evaluate the target lesions following image capture at the second timepoint 406). Following the first physician reviewer's segmentation of the target lesion at the second timepoint 408, the target lesion location file can be updated with a digital marker location at the second timepoint based on the target lesion segmentation data or other target lesion metrics.

Updating the digital marker location at each timepoint can be beneficial, as the target lesion may change in size (e.g., regress or grow) or shape between timepoints. For example, the central aspect of the target lesion may change due to shrinkage (or alternatively due to growth) of the target lesion between timepoints. Thus, the digital marker may potentially drift away from the target lesion if left in the same position over time. Once the digital marker location is updated within the target lesion location file or another entry is created within the target lesion location file indicating the location of the digital marker at the subsequent timepoints, the digital marker can then be displayed for each subsequent user at the proper location given the timepoint observed.

Figure 9:
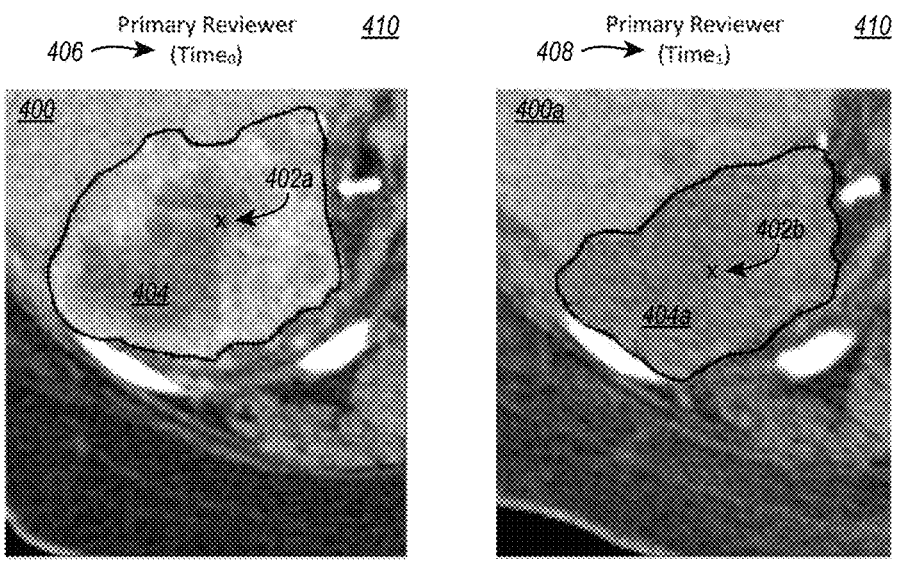
FIG. 9 illustrates the exemplary displays of FIG. 8 with the reviewer having segmented the illustrated target lesions at both time points using a freeform region-of-interest (ROI) tool.

An exemplary illustration of the foregoing is provided in FIG. 9. As shown, the location 402a of the digital marker (illustrated as an "X") at a first timepoint (Time$_0$) 406 is determined following segmentation of the target lesion 404 by the primary reviewer 410. By the second timepoint (Time$_1$) 408, the target lesion 404a has reduced in size, and the shape of the target lesion 404a has also changed compared to the same target lesion 404 at the first timepoint (Time$_0$) 406. As described above, the location 402a of the digital marker within the target lesion 404 can be determined based on a pre-selected target lesion metric. In the exemplary case of FIG. 9, the location 402a, 402b of the digital marker at the first 406 and second 408 timepoints is the central aspect of the segmented target lesion 404, 404a. Due to the change in size and shape of the target lesion 404, 404a between timepoints 406, 408, the central aspect additionally changed, causing a shift in the location 402a of the digital marker at the second timepoint 408.

Accordingly, in some embodiments, the primary reviewer 410 may open an analogous cross-sectional image 400a captured at the second timepoint 408 that includes the target lesion 404a. The digital marker can be placed at the original location 402a on the analogous cross-sectional image 400a (not shown) so that the primary reviewer can make the determination of which target lesion is to be measured. Following the primary reviewer's segmentation of the target lesion 404a, the updated location 402b of the digital marker can be determined and saved within the target lesion location file for later access by subsequent secondary reviewers.

In some embodiments, the physician reviewer may understand that the location of the digital marker is based on a given target lesion metric, and this may create a bias. To prevent such a bias, the location of the digital marker can be placed a random number of pixels away from the central aspect of the target lesion. For example, the placement of the digital marker can be randomly selected from any of 0-10 pixels away from the central aspect in a positive or negative x and y direction. An exemplary illustration of this includes the location of the digital marker being 4 pixels in the negative x direction and 2 pixels in the positive y direction of the determined central aspect of the target lesion or (−4, 2).

Additionally, or alternatively, the location of the digital marker can be determined, as above, for the first timepoint. Thereafter, the segmentation data for each primary and secondary reviewer can be used to determine the placement of the digital marker at each subsequent timepoint. For example, the segmentation data for each primary and secondary reviewer can be used to calculate an average location of the central aspect, and this average location can be used as the location for the digital marker at subsequent timepoints.

Figure 10:
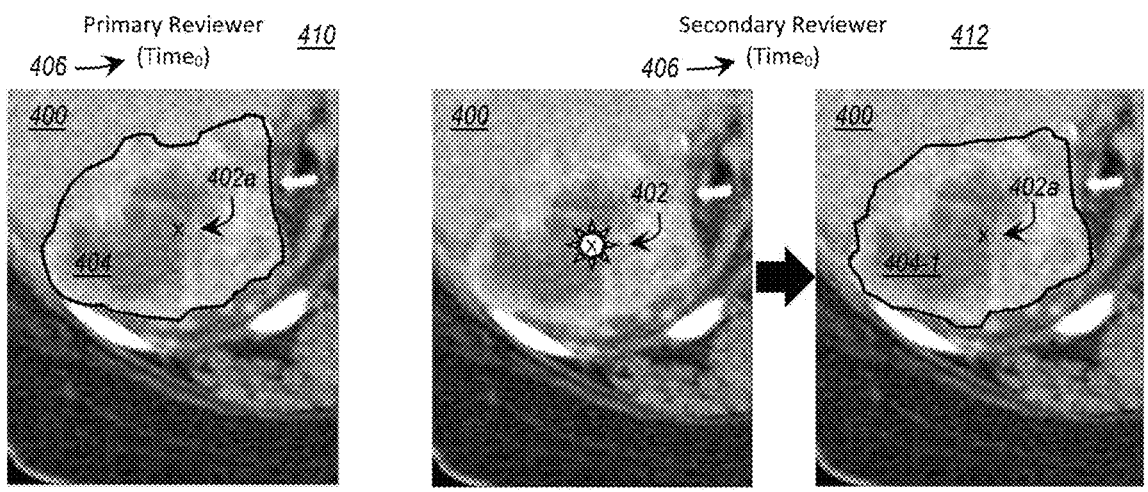
FIG. 10 illustrates an exemplary display of standardized target lesion selection where the same cross-sectional medical image at the same timepoint identifies a target lesion using a digital marker upon which each reviewer can draw a free-form region of interest (ROI) about the target lesion for subsequent lesion metric analysis.

As an additional example shown in FIG. 10, a primary reviewer 410 can segment a target lesion 404 at a first timepoint (Time$_0$) 406, and the location 402a of the digital marker can be determined based on the primary reviewer's segmentation of the target lesion. The digital marker 402 can be placed on the cross-sectional image 400 at the location 402a determined by the primary reviewer's segmentation of the target lesion 404. The secondary reviewer can segment the target lesion 404-1 according to their own interpretation (shown in FIG. 10 as a difference in target lesion boundaries between primary 410 and secondary 412 reviewers). Based on the segmentation of the target lesion 404-1 by the secondary reviewer 412, a secondary-reviewer-specific location can be determined and saved in the target lesion location file such that each reviewer has a personalized digital marker location at the second and subsequent timepoints that is based on the segmentation and target lesion metrics calculated at the previous timepoint. This and other methods can be implemented to reduce the potential for bias among the physician reviewers while still allowing the standardization of target lesion selection between physician reviewers and timepoints.

Computer-Implemented Methods for Standardizing Target Lesion Selection

FIGS. 1-10 and the corresponding text illustrate or otherwise describe one or more components, modules, mechanisms and/or detailed summary displays (also referred to herein as customizable summary images) for determining an objective tumor response to an anti-cancer therapy and standardizing target lesion selection using one or more cross-sectional images. One will appreciate that embodiments of the present disclosure can also be described in terms of methods comprising acts for accomplishing a particular result. For example, FIG. 11 and the corresponding text illustrate or otherwise describe a sequence of acts in a method for standardizing target lesion selection within cross-sectional medical images. The acts of FIG. 11 are described below with reference to the components and modules illustrated in FIGS. 1-10.

Figure 11:
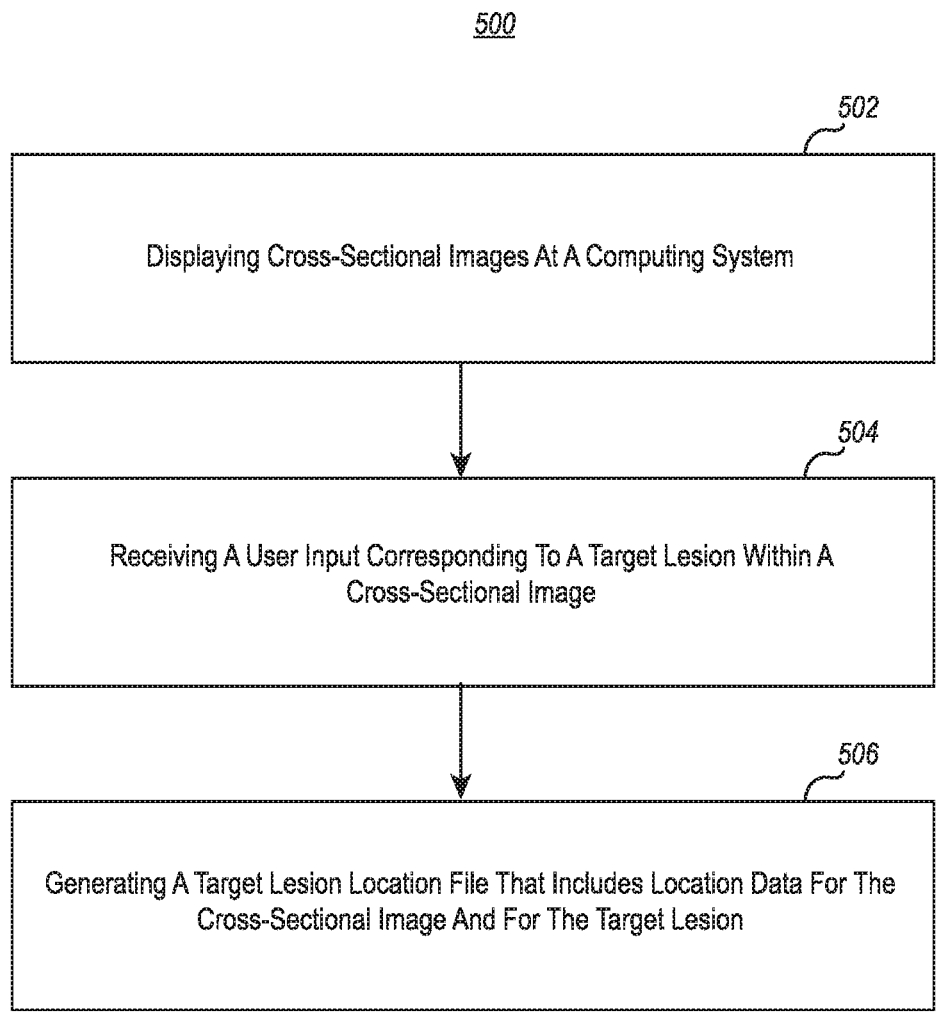
FIG. 11 illustrates a computer-implemented method of standardized target lesion selection in accordance with one or more embodiments of the present disclosure.

FIG. 11 shows a method 500 for standardizing target lesion selection within cross-sectional medical images includes an act 502 of displaying cross-sectional images at a computing system. Act 502 can include displaying a plurality of cross-sectional images at the computing system, each cross-sectional image comprising a cross-sectional slice of digital medical image data captured at a first timepoint from a radiologic device.

For example, computing system 100 of FIG. 1 can display cross-sectional images 102 received from a radiologic device 104 to a user using I/O device interfaces 106. It should be appreciated that this act—in addition to the other method acts discussed herein—can additionally be observed and practiced from a different perspective, such as from the perspective of a user or a user's device (i.e., receiving cross-sectional images at computing device 120*a*) or from the perspective of a server or control system (i.e., sending cross-sectional images to computing device 120*a* from computing system 100).

The method 500 can additionally include the act 504 of receiving a user input corresponding to a target lesion within a cross-sectional image. Act 504 can comprise receiving a user input identifying a set of pixels corresponding to a target lesion within a cross-sectional image of the plurality of cross-sectional images.

For example, computing system 100 can receive the user input through I/O device interfaces 106 that corresponds to a target lesion, such as the user segmenting the target lesion using a free-form region of interest tool. Through through image processing module 110 or hardware processor(s) 108, the computing system 100 can identify a set of pixels corresponding to a target lesion identified by the user input.

The method 400 can additionally include the act 506 of generating a target lesion location file that includes location data for the cross-sectional image and for the target lesion. Act 506 can comprise generating a target lesion location file comprising a precise anatomical location of the cross-sectional image and a pixel location of the target lesion within the cross-sectional image.

For example, computing system 100 can generate target lesion data 122 that includes the location data for the cross-sectional image and for the target lesion and can export the data as a target lesion location file using export module 118 through network 126 to a storage database system 124 that can be accessed later by computing system 100 or computing devices 120*a*, 120*b*, 120*c*, as necessary.

It should be appreciated that any of the other disclosed methods and method acts can similarly be executed using any of the modules and computing systems/devices disclosed in FIGS. 1-10, as appropriate and as understood by one having skill in the art.

Computing Devices of the Present Disclosure

In certain embodiments, the computer systems and modules disclosed herein include hardware, software and/or a combination of hardware and software. In some embodiments, software according to the present disclosure is operable offline, on a computer, on a server, on a cloud-based system and/or on a portable computing device. In some embodiments, the image display unit comprises, for example, a computer monitor, a television, and/or another display screen, as known in the art. In certain embodiments, the image data storage unit comprises a form of memory that is accessible via a computer. For example, in certain embodiments, the data storage unit comprises a hard drive, a removable disk, cloud-based storage, or any other memory unit known in the art. The methods of the present disclosure may be carried out on an image processing module. In certain embodiments, the image processing module comprises at least one of a digital capture apparatus, an image processing unit, an image display unit and/or an image data storage unit.

The methods disclosed herein are implemented by one or more computing systems. It will be appreciated that computing systems are increasingly taking a wide variety of forms. Computing systems may, for example, be handheld devices, appliances, laptop computers, desktop computers, mainframes, distributed computing systems, datacenters, or even devices that have not conventionally been considered a computing system, such as wearables (e.g., glasses). In this description and in the claims, the term "computer system" or "computing system" is defined broadly as including any device or system—or combination thereof—that includes at least one physical and tangible processor and a physical and tangible memory capable of having thereon computer-executable instructions that may be executed by a processor. The memory may take any form and may depend on the nature and form of the computing system. A computing system may be distributed over a network environment and may include multiple constituent computing systems.

In its most basic configuration, a computing system typically includes at least one hardware processing unit and memory. The memory may be physical system memory, which may be volatile, non-volatile, or some combination of the two. The term "memory" may also be used herein to refer to non-volatile mass storage such as physical storage media. The computing system may be a standalone or distributed system. If the computing system is distributed, the processing, memory, and/or storage capability may be distributed as well.

Any number and/or type of general purpose or special purpose computing systems described above can be configured to predict and/or modify resource utilization and demands. For example, the database(s) may be stored in the memory of computing system, and for the purpose of this disclosure, any general purpose or special purpose computer storing at least a portion of one or more databases will be generally referred to as a database server. It should be appreciated, however, that the term "database server" as used herein should also be understood to include the back-end system of a database application that performs tasks such as data analysis, storage, data manipulation, archiving, and other non-user specific tasks.

The computing system also has thereon multiple structures often referred to as an "executable component." For instance, the memory of the computing system is illustrated as including executable component. The term "executable component" is the name for a structure that is well understood to one of ordinary skill in the art in the field of computing as being a structure that can be software, hardware, or a combination thereof. For instance, when implemented in software, one of ordinary skill in the art would understand that the structure of an executable component may include software objects, routines, methods, and so forth, that may be executed by one or more processors on the computing system, whether such an executable component exists in the heap of a computing system, or whether the executable component exists on computer-readable storage media.

The structure of the executable component exists on a computer-readable medium in such a form that it is operable, when executed by one or more processors of the computing system, to cause the computing system to perform one or more function, such as the functions and methods described herein. Such a structure may be computer-readable directly by the processors—as is the case if the executable component were binary. Alternatively, the structure may be structured to be interpretable and/or compiled—whether in a single stage or in multiple stages—so as to generate such binary that is directly interpretable by the processors. Such an understanding of exemplary structures of an executable component is well within the understanding of one of ordinary skill in the art of computing when using the term "executable component."

The term "executable component" is also well understood by one of ordinary skill as including structures that are implemented exclusively or near-exclusively in hardware, such as within a field programmable gate array (FPGA), an application specific integrated circuit (ASIC), Program-specific Standard Products (ASSPs), System-on-a-chip systems (SOCs), Complex Programmable Logic Devices (CPLDs), or any other specialized circuit. Accordingly, the term "executable component" is a term for a structure that is well understood by those of ordinary skill in the art of computing, whether implemented in software, hardware, or a combination. In this description, the terms "component," "service," "engine," "module," "control," "generator," or the like may also be used. As used in this description and in this case, these terms—whether expressed with or without a modifying clause—are also intended to be synonymous with the term "executable component," and thus also have a structure that is well understood by those of ordinary skill in the art of computing.

In the description that follows, embodiments are described with reference to acts that are performed by one or more computing systems. If such acts are implemented in software, one or more processors (of the associated computing system that performs the act) direct the operation of the computing system in response to having executed computer-executable instructions that constitute an executable component. For example, such computer-executable instructions may be embodied on one or more computer-readable media that form a computer program product. An example of such an operation involves the manipulation of data.

The computer-executable instructions (and the manipulated data) may be stored in the memory of the computing system. The computing system may also contain communication channels that allow the computing system to communicate with other computing systems over, for example, a network.

While not all computing systems require a user interface, in some embodiments the computing system includes a user interface for use in interfacing with a user. The user interface may include output mechanisms as well as input mechanisms (collectively "I/O Devices" or similar). The principles described herein are not limited to the precise output mechanisms or input mechanisms as such will depend on the nature of the device. However, output mechanisms might include, for instance, speakers, displays, tactile output, holograms, and so forth. Examples of input mechanisms might include, for instance, microphones, touchscreens, holograms, cameras, keyboards, mouse, or other pointer input, sensors of any type, and so forth.

Accordingly, embodiments described herein may comprise or utilize a special purpose or general-purpose computing system. Embodiments described herein also include physical and other computer-readable media for carrying or storing computer-executable instructions and/or data structures. Such computer-readable media can be any available media that can be accessed by a general purpose or special purpose computing system. Computer-readable media that store computer-executable instructions are physical storage media. Computer-readable media that carry computer-executable instructions are transmission media. Thus, by way of example—not limitation—embodiments of the invention can comprise at least two distinctly different kinds of computer-readable media: storage media and transmission media.

Computer-readable storage media include RAM, ROM, EEPROM, solid state drives ("SSDs"), flash memory, phase-change memory ("PCM"), CD-ROM or other optical disk storage, magnetic disk storage or other magnetic storage devices, or any other physical and tangible storage medium which can be used to store desired program code in the form of computer-executable instructions or data structures and which can be accessed and executed by a general purpose or special purpose computing system to implement the disclosed functionality of the invention.

Transmission media can include a network and/or data links which can be used to carry desired program code in the form of computer-executable instructions or data structures and which can be accessed and executed by a general purpose or special purpose computing system. Combinations of the above should also be included within the scope of computer-readable media.

Further, upon reaching various computing system components, program code in the form of computer-executable instructions or data structures can be transferred automatically from transmission media to storage media (or vice versa). For example, computer-executable instructions or data structures received over a network or data link can be buffered in RAM within a network interface module (e.g., a "NIC") and then eventually transferred to computing system RAM and/or to less volatile storage media at a computing system. Thus, it should be understood that storage media can be included in computing system components that also—or even primarily—utilize transmission media.

Although the subject matter described herein is provided in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computing system configurations, including, personal computers, desktop computers, laptop computers, message processors, hand-held devices, multi-processor systems, microprocessor-based or programmable consumer electronics, network PCs, minicomputers, mainframe computers, tablets, mobile telephones, PDAs, pagers, routers, switches, datacenters, wearables (e.g., glasses) and the like. The invention may also be practiced in distributed system environments where local and remote computing systems, which are linked (either by hardwired data links, wireless data links, or by a combination of hardwired and wireless data links) through a network, both perform tasks. In a distributed system environment, program modules may be located in both local and remote memory storage devices.

Those skilled in the art will also appreciate that the invention may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud-computing model may also come in the form of various service models such as, for example, Software as a Service ("SaaS"), Platform as a Service ("PaaS"), and Infrastructure as a Service ("IaaS"). The cloud-computing model may also be deployed using different deployment models such as private cloud, community cloud, public cloud, hybrid cloud, and so forth.

All combinations of method or process steps as used herein can be performed in any order, unless otherwise specified or clearly implied to the contrary by the context in which the referenced combination is made.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computer system for standardizing target lesion selection within cross-sectional medical images, the computer system comprising:
   one or more processors; and
   one or more computer readable hardware storage devices, wherein the one or more computer readable hardware storage devices comprise computer-executable instructions executable by at least one of the one or more processors to cause the computer system to perform at least the following:
      send a plurality of cross-sectional images to a user device, each cross-sectional image comprising a cross-sectional slice of digital medical image data captured at a first timepoint from a radiologic device;
      receive a user input identifying a target lesion within a cross-sectional image of the plurality of cross-sectional images;
      generate a target lesion location file comprising a precise anatomical location of the cross-sectional image and a pixel location of the target lesion within the cross-sectional image;
      access a second plurality of cross-sectional images comprising cross-sectional slices of digital medical image data captured at a second timepoint;
      access the target lesion location file and based on the precise anatomical location of the cross-sectional image, identify an analogous cross-sectional image from the second plurality of cross-sectional images; and
      cause a digital marker to be displayed on the analogous cross-sectional image identifying an analogous area corresponding to the pixel location of the target lesion within the analogous cross-sectional image.

2. The computer system of claim 1, wherein the computer-executable instructions additionally cause the computer system to:
   receive one or more additional user inputs, each additional user input identifying an additional target lesion within the cross-sectional image or within an additional cross-sectional image of the plurality of cross-sectional images; and
   generate an updated target lesion location file additionally comprising precise anatomical locations for each additional cross-sectional image and respective pixel locations for each additional target lesion within the corresponding cross-sectional image or additional cross-sectional image.

3. The computer system of claim 2, wherein the computer-executable instructions additionally cause the computer system to identify or prompt a user to identify the target lesion and each of the additional target lesions in accordance with one or more tumor response criteria.

4. The computer system of claim 2, wherein the computer-executable instructions additionally cause the computer system to:
   access the updated target lesion location file and, based on the precise anatomical locations of each of the cross-sectional image and the additional cross-sectional images, identify a set of analogous cross-sectional images from the second plurality of cross-sectional images; and
   cause an additional digital marker to be displayed on each analogous cross-sectional image of the set of analogous cross-sectional images identifying an analogous area corresponding to the respective pixel location of the additional target lesions.

5. The computer system of claim 4, wherein the computer-executable instructions additionally cause the computer system to receive additional user input comprising segmentation data for the target lesion and the additional target lesions within the set of analogous cross-sectional images.

6. The computer system of claim 5, wherein the computer-executable instructions additionally cause the computer system to determine one or more target lesions metrics for the target lesion and each of the additional target lesions at the first timepoint and at the second timepoint.

7. The computer system of claim 6, wherein the computer-executable instructions additionally cause the computer system to update the updated target lesion location file with the one or more target lesion metrics.

8. The computer system as in claim 6, wherein, for the target lesion and each of the additional target lesions, the one or more target lesion metrics comprise one or more of:
   a longest dimension length;
   a short axis dimension length;
   a craniocaudal dimension length;
   a longest dimension length of vascularized tumor;
   a pixel area of a set of pixels defining the target lesion or the additional target lesion;
   a pixel volume of the set of pixels;
   a mean value of pixel intensities within the total range of pixel intensities;
   a mean value of pixel intensities within the subset of pixels;
   a maximum value of pixel intensities within the total range of pixel intensities;
   a histogram parameter, wherein the histogram parameter comprises a quantitative distribution of pixel intensities in the set of pixels; and
   a texture parameter, wherein the texture parameter comprises a first-, second- or third-order statistical characterization of pixel intensities in the set of pixels.

9. The computer system of claim 2, wherein the computer-executable instructions additionally cause the computer system to:

send the cross-sectional image and each of the additional cross-sectional images to a second user device; and cause an additional digital marker to be displayed on the cross-sectional image and on each of the additional cross-sectional images identifying the respective pixel location of the target lesion or the additional target lesions.

10. The computer system of claim 9, wherein the computer-executable instructions additionally cause the computer system to receive a second user input comprising segmentation data for the target lesion and the additional target lesions.

11. The computer system of claim 4, wherein the computer-executable instructions additionally cause the computer system to:

send the set of analogous cross-sectional images to a second user device; and cause the digital marker and the additional digital markers to be displayed on each analogous cross-sectional image of the set of analogous cross-sectional images identifying an analogous area corresponding to the respective pixel location of the target lesion or the additional target lesions.

12. The computer system of claim 11, wherein the computer-executable instructions additionally cause the computer system to receive an additional second user input comprising segmentation data for the target lesion and the additional target lesions within the set of analogous cross-sectional images.

13. The computer system of claim 12, wherein the computer-executable instructions additionally cause the computer system to determine one or more target lesions metrics for the target lesion and each of the additional target lesions at the first timepoint and at the second timepoint.

14. The computer system of claim 13, wherein the computer-executable instructions additionally cause the computer system to determine an objective tumor response based on the one or more target lesion metrics associated with the user and second user inputs.

15. A computer-implemented method for standardizing target lesion selection within cross-sectional medical images, comprising:

receiving a user input identifying a set of pixels within a across-sectional image captured at a first timepoint from a radiologic device, the set of pixels corresponding to a segmented target lesion;

generating a target lesion location file, wherein the target lesion location file comprises a precise anatomical location of the cross-sectional image and a pixel location of the target lesion;

accessing the target lesion location file and based on the precise anatomical location of the cross-sectional image, identifying an analogous cross-sectional image, the analogous cross-sectional image being captured at a second timepoint and comprising an analogous pixel location of the target lesion at an analogous precise anatomical location; and causing a digital marker to be displayed on the analogous cross-sectional image identifying the analogous pixel location of the target lesion.

16. The computer-implemented method of claim 15, further comprising:

receiving an authentication request from a second user;
accessing the target lesion location file;
displaying the cross-sectional image to the second user; and
displaying a digital marker at the central aspect of the target lesion on the cross-sectional image.

17. The computer-implemented method of claim 15, further comprising determining one or more target lesion metrics of the segmented target lesion.

18. The computer-implemented method of claim 17, further comprising executing the method act recited in claim 17 for a plurality of additional target lesions at any of the first timepoint, the second timepoint, or one or more additional timepoints.

19. A computer program product comprising one or more computer readable hardware storage devices having stored thereon computer-executable instructions that are structured such that, when executed by one or more processors of a computing system, a computing system is configured to perform a method for standardizing target lesion selection within cross-sectional medical images, the method comprising:

displaying a plurality of cross-sectional images at the computing system, each cross-sectional image comprising a cross-sectional slice of digital medical image data captured at a first timepoint from a radiologic device;

receiving a user input identifying a target lesion within a cross-sectional image of the plurality of cross-sectional images;

generating a target lesion location file comprising a precise anatomical location of the cross-sectional image and a pixel location of the target lesion within the cross-sectional image;

accessing the target lesion location file and based on the precise anatomical location of the cross-sectional image, identifying an analogous cross-sectional image from a second plurality of cross-sectional images captured at a second timepoint, the analogous cross-sectional image comprising an analogous pixel location of the target lesion; and displaying a digital marker on the analogous cross-sectional image identifying the analogous pixel location of the target lesion.

20. The computer program product of claim 19, wherein the method additionally comprises:

receiving a second user input identifying an additional target lesion within an additional cross-sectional image;

generating an updated target lesion location file comprising an additional precise anatomical for the additional cross-sectional image and a respective pixel location for the additional target lesion.

* * * * *

UNITED STATES PATENT AND TRADEMARK OFFICE
CERTIFICATE OF CORRECTION

PATENT NO. : 10,219,768 B2  
APPLICATION NO. : 16/003707  
DATED : March 5, 2019  
INVENTOR(S) : Andrew Dennis Smith Page 1 of 1

It is certified that error appears in the above-identified patent and that said Letters Patent is hereby corrected as shown below:

In the Specification

Column 1  
Line 45, change "measures cm" to –measures $\geq 1.0$ cm–  
Line 47, change "measures cm" to –measures $\geq 1.5$ cm–

Column 3  
Line 46, change "obtaining accurate" to –obtaining an accurate–

Column 4  
Line 65, change "identifies" to –identify–

Column 6  
Line 7, delete "a"

Column 15  
Line 53, remove [that]  
Line 56, change "his" to –is–

Column 18  
Line 67, change "includes" to –including–

Column 19  
Line 27, remove second instance of [through]

Signed and Sealed this  
Third Day of March, 2020

Andrei Iancu  
*Director of the United States Patent and Trademark Office*